(12) United States Patent
Lorenz et al.

(10) Patent No.: US 8,822,721 B2
(45) Date of Patent: Sep. 2, 2014

(54) METHOD FOR SEPARATION OF RACEMIC COMPOUND-FORMING CHIRAL SUBSTANCES BY A CYCLIC CRYSTALLIZATION PROCESS AND A CRYSTALLIZATION DEVICE

(75) Inventors: Heike Lorenz, Magdeburg (DE); Daniel Polenske, Egeln (DE); Linzhu Klukas, Magdeburg (DE); Andreas Seidel-Morgenstern, Magdeburg (DE)

(73) Assignee: Max-Planck-Gesellschaft zur Förderung der Wissenschaften e.V., Munich (DE)

( * ) Notice: Subject to any disclaimer, the term of this patent is extended or adjusted under 35 U.S.C. 154(b) by 182 days.

(21) Appl. No.: 13/368,638

(22) Filed: Feb. 8, 2012

(65) Prior Publication Data

US 2012/0197040 A1 Aug. 2, 2012
US 2013/0184489 A2 Jul. 18, 2013

Related U.S. Application Data

(63) Continuation of application No. PCT/EP2010/062682, filed on Aug. 31, 2010.

(30) Foreign Application Priority Data

Sep. 2, 2009 (EP) .................................. 09169202

(51) Int. Cl.
*C07B 55/00* (2006.01)
*C07B 57/00* (2006.01)
*B01D 9/00* (2006.01)

(52) U.S. Cl.
CPC ............ *C07B 57/00* (2013.01); *C07B 2200/01* (2013.01); *B01D 9/0013* (2013.01)
USPC ...................................................... 562/402

(58) Field of Classification Search
CPC ............................ C07B 55/00; C07B 2200/01
USPC ....................................................... 562/402
See application file for complete search history.

(56) References Cited

U.S. PATENT DOCUMENTS

| 326,687 | A | 9/1885 | Sparks |
| 3,266,871 | A | 8/1966 | Mizoguchi Naomasa et al. |
| 6,022,409 | A | 2/2000 | Coquerel et al. |
| 7,132,570 | B2 | 11/2006 | Neckebrock et al. |
| 2008/0207944 | A1 | 8/2008 | Seidel-Morgenstern et al. |

FOREIGN PATENT DOCUMENTS

| DE | 1 418 567 | 10/1968 |
| GB | 1 273 278 | 5/1972 |
| JP | 55-115846 | 9/1980 |
| JP | 61-148156 | 7/1986 |
| JP | 06-340599 | 12/1994 |
| JP | 09-066202 | 3/1997 |
| JP | 09-506861 | 7/1997 |
| JP | 2006-511588 | 4/2006 |
| WO | WO 2007/023129 | 3/2007 |

OTHER PUBLICATIONS

Office Action, Japanese Patent Application No. 2012-527298, Aug. 9, 2013, 4 pages.
Office Action, Japanese Patent Application No. 2012-527298, Aug. 9, 2013, 4 pages, English Translation.
European Search Report for European Application No. 09 16 9202, completed Feb. 18, 2010.
International Search Report for PCT/EP2010/062682, mailed Dec. 6, 2010.
International Preliminary Report on Patentability for PCT/EP2010/062682, issued Mar. 6, 2012.

*Primary Examiner* — Shawquia Young
(74) *Attorney, Agent, or Firm* — Lathrop & Gage LLP

(57) ABSTRACT

The invention concerns a method for separating a racemic compound-forming chiral substance by a cyclic crystallization process which is conducted in at least one first crystallization unit (10) and in at least one second crystallization unit (18), wherein in a first process cycle an enantiomer is crystallized in the first crystallization unit (10) and a racemic compound is crystallized in the second crystallization unit (18), wherein in a second process cycle the enantiomer is crystallized in the second crystallization unit (18) and the racemic compound is crystallized in the first crystallization unit (10), wherein during each process cycle in at least one process sub-step (B→C, F→G) a mother liquor (12) being contained in the first crystallization unit (10) is mutually exchanged with a mother liquor (20) being contained in the second crystallization unit (18). An auto-seeding process sub-step is applied at the beginning of a process cycle.

21 Claims, 4 Drawing Sheets

METHOD FOR SEPARATION OF RACEMIC COMPOUND-FORMING CHIRAL SUBSTANCES BY A CYCLIC CRYSTALLIZATION PROCESS AND A CRYSTALLIZATION DEVICE

CROSS-REFERENCE TO RELATED APPLICATION

This application is a continuation of International Application No. PCT/EP2010/062682, filed Aug. 31, 2010, which claimed the benefit of priority from European Patent Application No. 09 169 202.0, filed Sep. 2, 2009, each of which is hereby incorporated by reference in its entirety.

DESCRIPTION

The present invention relates to a method for separation of compound-forming chiral substances by a cyclic crystallisation process, which is conducted in at least one first and in at least one second crystallization unit, wherein in a first process cycle an enantiomer is crystallized in the first crystallization unit and a racemic compound is crystallized in the second crystallization unit.

Chiral substances are optical active molecules which have the ability to rotate plane-polarized light. These molecules exist in two different stereoisomeric forms which are non-super-imposable mirror images of each other and are so-called enantiomers and counter-enantiomers. These two types of enantiomers have identical chemical and physical properties but often have different effects on biological entities.

A mixture of an equimolar composition of enantiomers and counter-enantiomers is called a racemate while racemic compounds are available in a crystal structure with an equimolar composition of optical active enantiomers and counter-enantiomers in an ordered ratio within the elementary cell.

In pharmaceutical, agrochemical and allied industries there is a growing demand for chiral molecules for processing drugs, food and fragrance, especially for those enantiomers, which have the desired properties. In particular the separation of pure enantiomers from racemic compounds has a high economic potential since the majority of available chiral substances is existent as racemic compound. However in comparison to conglomerate systems, mixtures of compound-forming systems reveal an additional stable solid phase in their solubility characteristics, which inhibits the possibility for a direct crystallization, i.e. to obtain both enantiomers at the same time.

The enantioselective separation of racemic compound-forming mixtures is known from the state of the art. A generally recognized method for separation of racemic compounds is the preferential crystallization which can be applied to selectively obtain the desired enantiomer. A required starting point for application of a preferential crystallization to obtain a desired pure enantiomer and/or a racemic compound as a by-product is basically a saturated solution, which is enriched with the desired enantiomer.

WO 2007/023129 A2 relates to a hybrid method for the cyclic crystallization of enantiomers from compound-forming systems in one crystallization unit, i.e. a batch-wise mode. Based on an initial enrichment process step to provide a mixture with a certain enantiomeric excess close to the eutectic composition, preferential crystallization is applied. The solution then is supersaturated by cooling down the temperature and afterwards seeded with crystals of the desired enantiomer, which initializes the crystallization of the desired pure enantiomer. After gaining the solid enantiomer by filtration and addition of fresh feed, the clear supersaturated solution is seeded with crystals of the racemic compound and the racemic compound as a by-product is crystallized. The enantiomer and the racemic compound are produced alternatingly and successively in one crystallization unit. Therefore the productivity of this process is limited since only in every second cycle the desired pure enantiomer can be obtained.

In addition the concentration of the desired species in the mother liquor, i.e. in the liquid phase, is typically decreasing during this batch wise operated process, since the quantity of crystallized enantiomers or racemic compound is more and more increasing, while the concentration of the opposite species does not change. Consequently, the driving force (supersaturation) for the crystallization decreases with the progress of the process while there is an increasing tendency of nucleation of the counter-species, which has also a negative impact on productivity of the process and on yield, purity and quality of the final product. Furthermore separately produced seed crystals need to be added after each restart of the process cycle to initialize another crystallization cycle.

It is therefore an object of the present invention to provide a method for an efficient separation of enantiomers of a racemic compound-forming chiral substance while improving the disadvantages known from the state of the art and which is itself a simple and inexpensive method.

Another object is to provide a universal applicable method for an efficient production of a desired enantiomer while the productivity, yield and purity is increased and while an auto-seeding technique eliminates the problems connected with a separate seed addition.

A further object of the present invention is to provide a crystallization device for application of a method according to the present invention, with at least two crystallization units, which are coupled via liquid phases by mutual exchange of mother liquors.

According to the invention, this is achieved by a method and a device according to the independent claims. Further embodiments of the invention are subject matter of the dependent claims.

The invention concerns a method for a cyclic separation of a compound-forming substance, while the technique of preferential crystallization is applied. The inventive method starts up from at least two crystallization units which are hydraulically coupled. With the definition of a crystallization unit, e.g. a container, a tank, a reactor or a further vessel might be supposed, which is intended to receive a liquid mixture, a liquid phase or a suspension.

The hydraulically coupling of the above mentioned two crystallization units is realized for example by means of supply pipes and which are hydraulically connecting the interior of both crystallization units for the intended exchange of a liquid.

The liquid phases in both crystallization units are mutually, exchanged for example by means of two pumps or by means of the force of gravity. The so-called mother liquor of the first crystallization unit is transferred to the second crystallization unit, while the mother liquor of the second crystallization unit is transferred to the first crystallization unit. Thereby the liquid phase is exchanged at a certain or infinitely high rate.

The advantage of the exchange of the liquid phases in both crystallization units can be explained from a thermodynamic point of view. In the uncoupled case, the concentration of the desired species, which are intended to be crystallized in the mother liquor, in general is decreasing when the crystallization process is in progress, while the concentration of the counter-species remains constant.

As explained above, the degree of supersaturation in the mother liquor is the driving force for crystallization, i.e. the crystallization rate is in the uncoupled case permanently decreasing.

However, when at least two crystallization units are advantageously coupled with each other, the concentration of the respective counter-species is permanently decreased. Thus the probability for a nucleation of the undesired opposite species is notable reduced. Contrary, compared to the uncoupled case, the concentration of the desired species in the mother liquor is increased. Thus the coupling of two crystallization units leads to a higher crystallization rate, a higher productivity and product mass.

Preferably the method according to the invention comprises a separate or a parallel crystallization process of the desired enantiomer and the racemic compound in the at least two crystallization units. It has to be noted that a simultaneous or a non-simultaneous operation mode of the at least two crystallization units is possible.

For example the crystallization process in the first crystallization unit is started previously before the crystallization process in the second crystallization unit is started, i.e. is operated time-shifted. Imaginable is also a partly simultaneous operation mode, whereby for example a process sub-step of a crystallization processes is initialized in the second crystallization unit, when another process sub-step in the first crystallization unit is finished or has reached a certain condition.

In a preferred method the process cycle is operated several times, i.e. in a cyclic and/or in a continuous manner, while in each of the both crystallization units the enantiomer and the racemic compound is crystallized in an alternating manner.

Preferably the process according to the invention may be repetitively operated without the necessity to separately introduce seed crystals to initiate a subsequent crystallization process. In addition the crystallization can be performed as a cooling crystallization, i.e. the temperature of the mother liquor is decreased continuously during the crystallization process in order to optimally affect the degree of supersaturation which results in a higher crystallization rate.

In a preferred embodiment of the claimed method the two or more separate crystallization units are coupled via the liquid phase when the crystallization process is operated in proximity to the eutectic composition. Therefore the probability of the risk for a nucleation of the respective counter-species is reduced, while the purity is increased.

It is possible and desirable to use exchange flow-rates adjusted to the specific crystallization process occurring in the two crystallization units. This might be realized by an on-line or an off-line measurement of the physical and chemical conditions in the mother liquors and controlled by a process parameter. For example the enantiomeric excess in the first crystallization unit and/or in the second crystallization unit is monitored, while the exchange flow rates of the mother liquors is adapted accordingly to a certain rate.

In a further preferred embodiment of the claimed method a so-called entrainment process sub-step, wherein the exchange of mother liquors is interrupted, advantageously enriches the mother liquors with the respective counter species in each crystallization unit. This enrichment is advantageously used to generate the desired seed crystals for the initialization of a subsequent crystallization process cycle.

In a preferred embodiment of the invention a so-called auto-seeding process sub-step is comprised. After the feeding with eutectic feed material to the crystallization units to generate new initial suspension for the crystallization process sub-steps, during the auto-seeding process sub-step the temperature of the mother liquor is increased in order to selectively dissolve the opposite species, while the desired seed crystals remain present in the suspension. In addition, the mother liquor then is tempered to a certain temperature in order to ensure the equilibrium condition, i.e. just pure crystals of the desired species remain in the mother liquor.

In a preferred embodiment of the method, the process comprises several process sub-steps which can be operated repetitively in a closed process cycle and which are performed in a successive sequence in each of the both crystallization units separately. An individual operation order or the omission of at least one of the described process sub-steps is possible, but might lead to a sub-optimal operation of the process.

Further advantages and embodiments will be demonstrated by the enclosed drawings:

FIG. 1 schematically illustrates the crystallization device with two crystallization units according to the invention;

Figure 1:
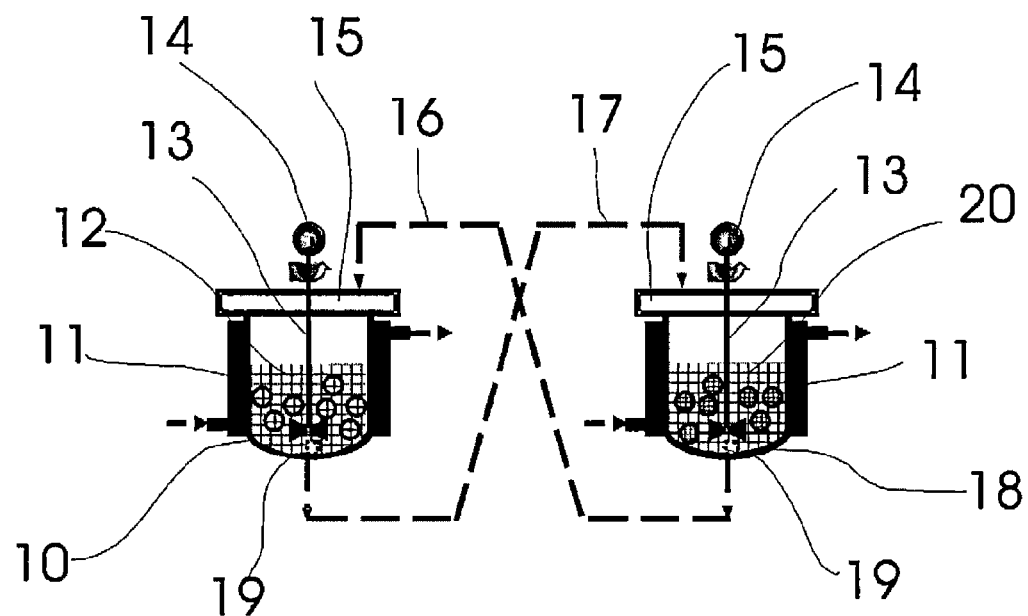

FIG. 1 shows the crystallization device with two crystallization units 10,18, which are coupled via the liquid phase. The first crystallization unit 10 and the second crystallization unit 18 are connected with each other via exchange pipes 16, 17. The first crystallization unit (10) is filled with the mother liquor (12) and the second crystallization unit is filled with the mother liquor (20). To guarantee the exchange of solid-free mother liquor from one crystallization unit to the other crystallization unit, each crystallization unit is equipped with an internal filter unit (19).

To obtain a thorough mixing each crystallization unit is equipped with a stirrer (13) and a driving unit (14). To ensure a rapid cooling-down and heating-up of the mother liquor, during polythermal operation mode, both crystallization units are equipped with a cooling-/heating-jacket (11), which is supplied by a liquid heat transfer medium.

Figure 2:
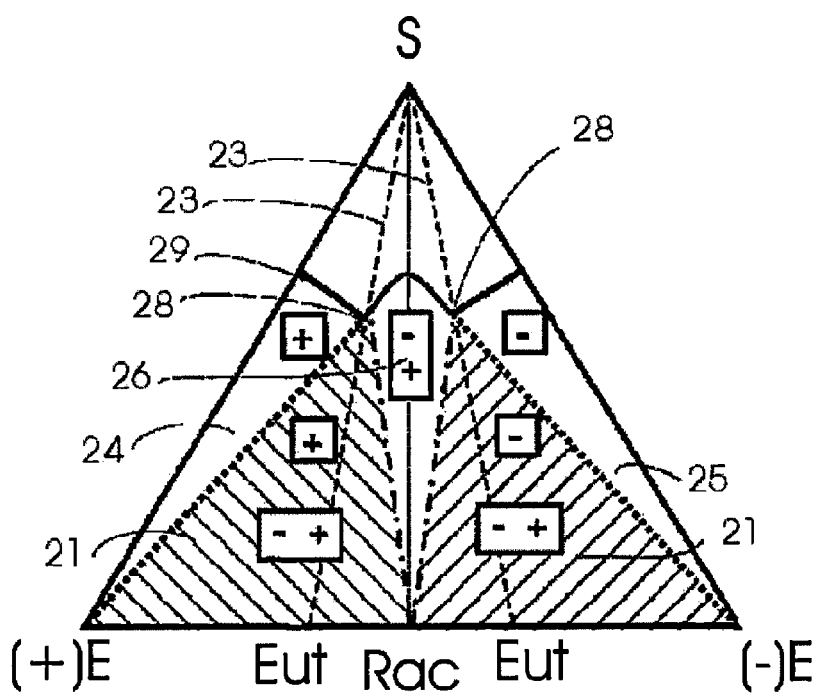
FIG. 2 shows a ternary phase diagram with 6 different phase areas for the racemic compound-forming system.

A crystallization-based separation process is most suitable to be demonstrated in a ternary phase diagram which characterizes the different solid/liquid phases of a ternary substance system. FIG. 2 shows schematically the ternary solubility phase diagram of two enantiomers (+)-E and (−)-E for a racemic compound-forming system and a solvent S. The dashed lines, which run from the binary eutectic compositions Eut to the top corner point S of the triangular diagram represent the so-called eutectic lines 23. Reference Rac on the bottom edge of the diagram denotes the racemic composition. The solubility isotherm 29 has five distinctive points (enantiomers, racemic compound and 2 eutectic points). Compound-forming substance systems are characterized in that an intermediate racemic compound is formed and therefore the area below the solubility isotherm is divided into five phase areas. Three two-phase regions and two three-phase regions exist below the solubility isotherm.

In the three two-phase regions 24, 25, 26, stable solid phases of the (+)-E enantiomer in region 24, the (−)-E enantiomer in region 25 or the racemic compound in region 26 are in equilibrium with the corresponding saturated liquid phases.

In the two three-phase regions 21 the enantiomers (+)-E or (−)-E and the racemic compound coexist while the enantiomer (+)-E or (−)-E and the racemic compound as solid phases are in equilibrium with a saturated liquid of eutectic composition.

To separate either the (+)-E or the (−)-E enantiomer from a racemic compound the two three-phase regions 21 of the ternary phase diagrams are interesting and applied for the method of preferential crystallization according to this invention.

The following described theoretical separation process cycle is exemplarily described on the (+)-E-side of the ternary phase diagram (FIG. 3), whereas the separation process can be applied on the (−)-E-side of the diagram accordingly to gain the (−)-E enantiomer.

Figure 3:
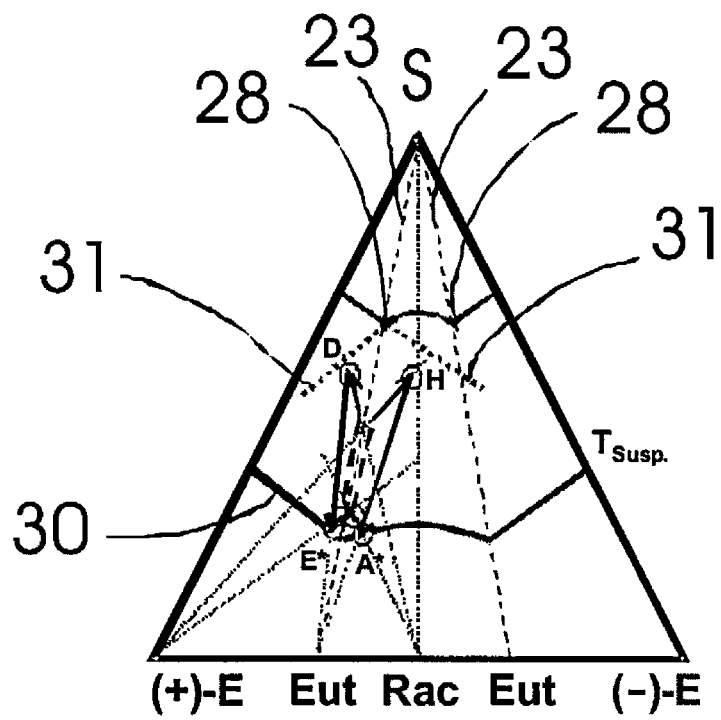
FIG. 3 shows the relevant crystallization trajectories in a ternary phase diagram according to the invention.
Figure 3B:
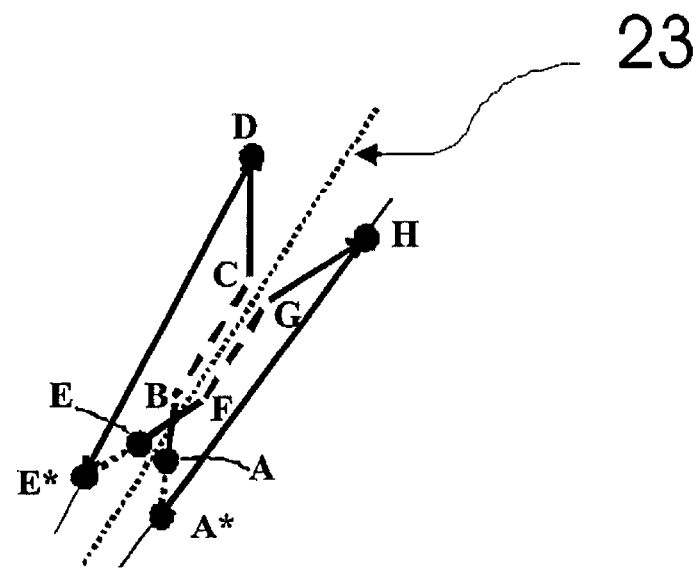

FIG. 3b shows a detailed view of the relevant process trajectories shown in FIG. 3, which are described below.

Figure 4:
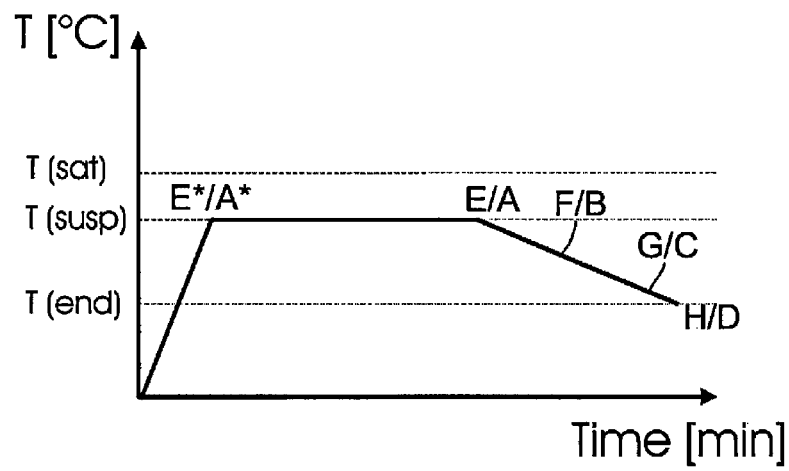
FIG. 4 shows a theoretical temperature profile for a process according to the invention.

The theoretical temperature profile of the described process is shown in FIG. 4.

To start-up the process according to the preferred method of the invention, enriched quasi-eutectic material is fed into both crystallization units 10, 18. Super-eutectic material, i.e. a mixture having a composition on the enantiomer side of the eutectic line, is feeded in crystallization unit 10 and sub-eutectic material, i.e. a mixture having a composition on the racemic compound side of the eutectic line, is feeded in crystallization unit 18 and is tempered at a temperature T (susp) together with the solvent. As a consequence, in crystallization unit 10 (+)-E-enantiomer crystals are present and in crystallization unit 18 crystals of the racemic compound are present (points A*/A and E*/E in FIG. 3b and FIG. 4). These crystals are used as seed crystals.

The so-called auto-seeding step is executed between the trajectory points A*→A and E*→E in both crystallization units (10,18) accordingly. At the start-up of such a cyclic process alternatively one can start with eutectic mixtures and once add seeds of (+)-E in crystallization unit 10 and racemic compound crystals in crystallization unit 18 to initialize the process cycle for the very first time, while the successive process cycles are self-seeded by the auto-seeding process sub-step.

During this auto-seeding step the not desired counter-species are selectively dissolved by tempering the suspension to a certain temperature limit T (susp) which is below the saturation temperature limit T (sat). Thus the seed crystals of the desired species are generated in the crystallization units (10, 18) and the starting points A and E are reached.

The temperature of both suspensions then is reduced at a certain cooling rate and the crystallization process is started due to the supersaturation (FIG. 4). Racemic compound crystallizes in crystallization unit 18 according to the theoretical crystallization trajectory A→B. (+)-E crystallizes accordingly in crystallization unit 10 (point E→F). After exceeding the eutectic line (point B and F), the mutually exchange of the liquid mother liquors is started at a certain exchange rate (point B→C and F→G), which results in a reduction of the supersaturation of the respective counter-species in the mother liquors while the crystallization rate of the desired species is increased. Then the selective crystallization process is operated under optimal conditions, in proximity to the eutectic line.

At points C and G the mutual exchange of the mother liquors is stopped and the crystallization processes are continued by a so-called entrainment step in both crystallization units (10,18). As a result, besides to the crystallization of the desired (+)-E-enantiomer in crystallization unit 10 and of the racemic compound in the crystallization unit 18, the mother liquor enriches with the respective counter-species. At points D and H both crystallization processes are stopped and the solid end products are gained from both crystallization units (10,18). The mother liquor 12 in the first crystallization unit 10 is enriched with racemic compound and the mother liquor (20) in the second crystallization unit 18 is enriched with enantiomer. New eutectic feed is added to both mother liquors in crystallization unit 10 and 18 and the starting points A* and E* (or A and E) are reached again. Now in crystallization unit 10 racemic compound and in crystallization unit 18 pure (+)-E enantiomer is gained in the next process cycle.

The following example process refers to the separation of racemic mandelic acid from a liquid aqueous solution whereas the desired target enantiomer is (+S)-mandelic acid. Of course the method according to the invention can be applied to further compound-forming substance systems, too. Novel application fields of the invention are further substances with eutectic characteristics like Alanin, Valin, Ibuprofen, Nitrendipin, Pseudoephedrin, Atenolol.

Both crystallization units are operated simultaneously. The experiment is started by preparation of differently enriched quasi-eutectic aqueous mixtures. Crystallization unit 10 is feeded with 300 g of an super-eutectic mixture of S-mandelic acid and racemic mandelic acid and crystallization unit 18 is feeded with 300 g of a sub-eutectic mixture of racemic mandelic acid and (S)-mandelic acid. The initial enantiomeric excess [ee] for the S-mandelic acid and racemic mandelic acid were set to ee=42% and ee=38% while the eutectic composition has an enantiomeric excess of ee=40%.

Figure 5:
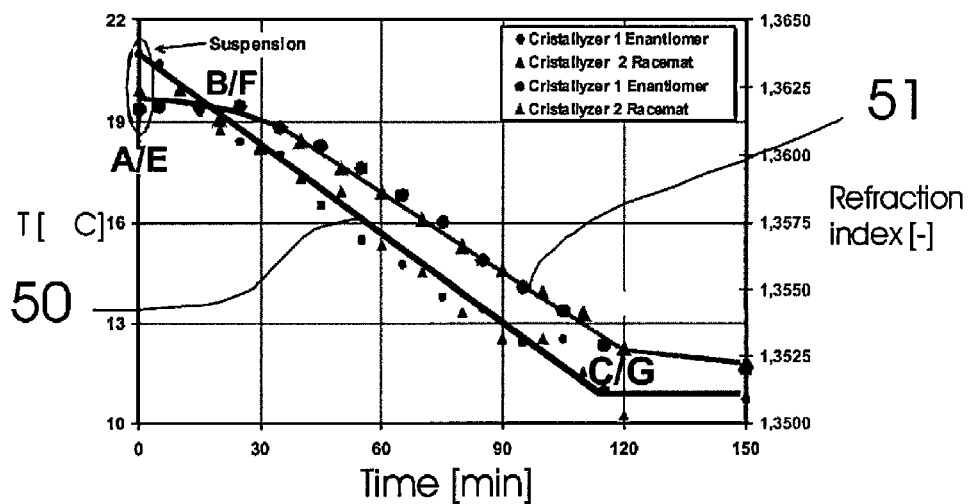
FIG. 5 shows the temperature and concentration profile in crystallization unit 10 and 18 as function of time for an example process, i.e. the mandelic acid/water system.

The internal conditions in both crystallization units are depicted in FIG. 5. The measured temperature profiles 50 and the trend of the refraction index 51 indicates the degree of supersaturation in the solution over the process course A/E→C/G in both crystallization units.

Both mixtures are initially tempered at 21° C. (before time zero in FIG. 5) while the respective counter-species are selectively dissolved to generate a sufficient excess of the desired seed crystals. The starting points A and E are reached. At that time the mixtures are cooled down successively in both crystallization units (10,18) at a cooling rate of 0.1° C./min (point A→C, E→G).

S-mandelic acid crystallizes in first crystallization unit 10 while racemic mandelic acid is crystallized in second crystallization unit 18. At a temperature of about 20° C. both mother liquors have an eutectic composition of the enantiomers (intersection point of trajectories AB and EF in FIG. 3). During the cooling phase S-mandelic acid and racemic mandelic acid are crystallizing continuously in the crystallization units 10 and 18.

When the exchange of the mother liquors is initialized (points B and F at a temperature of about 19° C. after about 20 minutes) the kinetics of the crystallization is improved, what can be clearly identified by the change of the slope in the concentration profile. The crystallization rate is increased and also stable until the process sub-step is interrupted at points G and C at a temperature of about 11° C.

Figure 6:
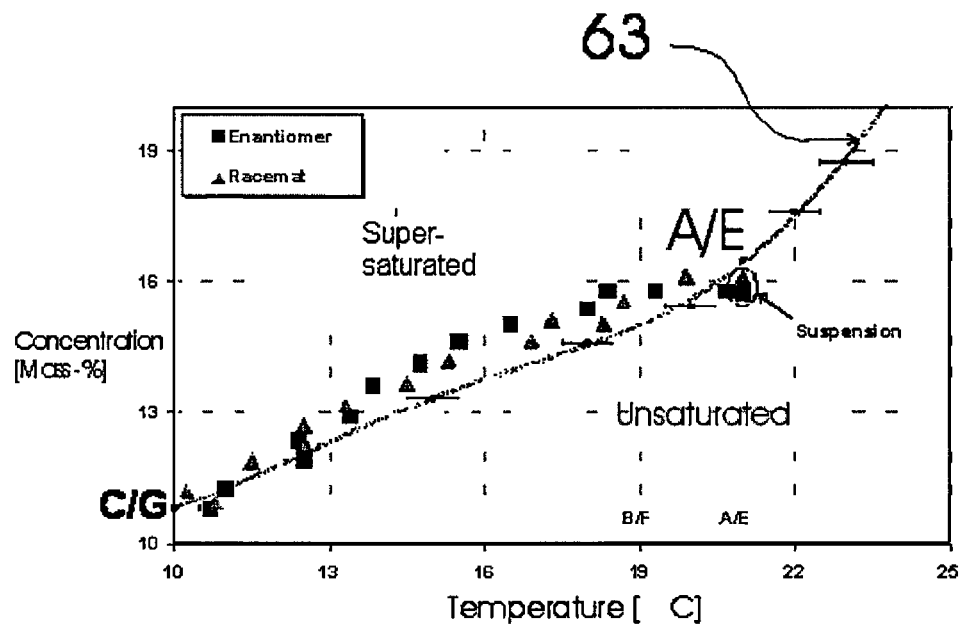
FIG. 6 shows the concentration profile of S- and racemic mandelic acid in crystallization unit 10 and 18 as a function of the temperature.

FIG. 6 demonstrates the concentrations of the S-mandelic acid and racemic mandelic acid during the crystallization in both crystallization units with reference to the eutectic composition. It can be seen that the concentration course of both species follows the eutectic line with only moderate supersaturations, also with reference to the respective counter-species.

Figure 7:
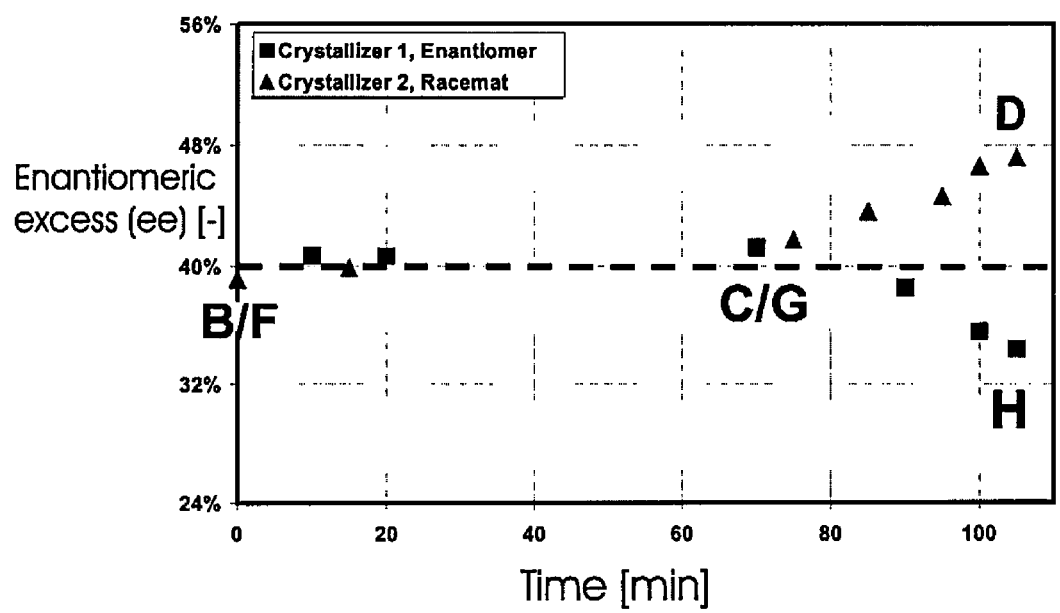
FIG. 7 shows the enantiomeric excess as a function of the time for an example process, i.e. the mandelic acid/water system.

FIG. 7 characterizes the enantiomeric excess of the process course during the steps B→D and F→H for the racemic compound and the (S)-enantiomer of mandelic acid in a further experiment. Initially the enantiomeric excess is kept stable corresponding to eutectic composition in both crystallization units. When the exchange of mother liquors is stopped after 70 minutes (point C/G) the entrainment step is subsequently executed, i.e. the counter-species are enriched in the mother liquors. While the enantiomeric excess is decreasing, S-mandelic acid is further on crystallizing in crystallization unit 10 and racemic mandelic acid is further on crystallizing in crystallization unit 18 while the enantiomeric excess is increasing. The process is stopped at points D and H and the gained products are filtered off.

The purity of the gained (S)-enantiomer and the racemic compound of mandelic acid were more than 96% and more than 99% respectively. The final solid products are obtained with about 25 g of racemic compound and about 17 g of S-mandelic acid which corresponds to a yield of 4% for racemic compound and 3% for S-mandelic acid.

The mother liquors of both crystallization units contained the respective counter-species with an enantiomeric excess of ee=6 to 7%.

By feeding both crystallization units with new eutectic material a subsequent cycle once more can be initiated by an in-situ generation of seed crystals by another auto-seeding process step.

The research of the applicant has shown that the method of a cyclic separation of a racemic compound-forming chiral substance system by means of an auto-seeded simultaneous preferential operation is feasible and provides stable process conditions.

The invention according to the invention offers a safe process regime with only moderate supersaturations of the undesired counter-species, since the process is conducted close to the eutectic equilibrium. By the exchange of mother liquors the nucleation of the respective undesired species can be avoided. Therefore a method is provided, to produce high-qualitative products with respective high purity and yield while the productivity is increased. When the method is performed in a multiple cycle, i.e. when several process cycles are performed successively, no further adding of seed crystal seeds is required.

LIST OF REFERENCES

10 First crystallization unit
11 Cooling-/heating-jacket
12 Mother liquor, crystallization unit
13 Stirrer
14 Motor/driving unit
15 Lid
16 Exchange pipe, second crystallization unit
17 Exchange pipe, first crystallization unit
18 Second crystallization unit
19 Filter unit
20 Mother liquor, second crystallization unit
21 Three-phase areas, ((+/−)E enantiomer and racemic compound)
23 Eutectic line
24 Two-phase area, (+)-E enantiomer
25 Two-phase area, (−)-E enantiomer
26 Two-phase area, racemic compound
28 Eutectic point
29 Solubility isotherm
31 Metastable solubility line
50 Temperature profile, first and second crystallization unit
51 Refraction index, first and second crystallization unit
63 Saturation line eutectic composition of the enantiomers
A*, E* Process start points
A, B, C, D Process points of racemic compound crystallization
E, F, G, H Process points of enantiomer crystallization
ee enantiomeric excess [−]
Rac Racemat
S Solvent
T (susp) Temperature of suspension
T (sat) Temperature of saturation
T (end) Temperature at end of crystallization

What is claimed is:

1. A method for crystallizing an enantiomer of a racemic compound-forming chiral substance comprising a cyclic crystallization process which is conducted in at least one first crystallization unit and in at least one second crystallization unit, wherein in a first process cycle an enantiomer is crystallized in the first crystallization unit and a racemic compound is crystallized in the second crystallization unit, wherein in a second process cycle the enantiomer is crystallized in the second crystallization unit and the racemic compound is crystallized in the first crystallization unit, wherein during each process cycle in at least one process sub-step a mother liquor in the first crystallization unit is mutually exchanged with a mother liquor in the second crystallization unit.

2. The method according to claim 1, wherein the cyclic crystallization process conducted in the first crystallization unit and the cyclic crystallization process conducted in the second crystallization unit are operated simultaneously.

3. The method according to claim 1, wherein the cyclic crystallization process conducted in the first crystallization unit and the cyclic crystallization process conducted in the second crystallization unit are operated non-simultaneously.

4. The method according to claim 1, wherein the temperature of the mother liquor in the first crystallization unit and/or the second crystallization unit is reduced during at least one crystallization process sub-step.

5. The method according to claim 1, wherein a continuous mutual exchange of the mother liquors between the first crystallization unit and the second crystallization unit is carried out.

6. The method according to claim 1, wherein a discontinuous mutual exchange of the mother liquors between the first crystallization unit and the second crystallization unit is carried out.

7. The method according to claim 5, wherein the mutual exchange of the mother liquors between the first crystallization unit and the second crystallization unit is carried out by a varying exchange flow rate.

8. The method according to claim 7, wherein the exchange flow rate is controlled by a process parameter, measured in at least one of the mother liquors.

9. The method according to claim 1, wherein the process sub-step of the mutual exchange of the mother liquors between the first crystallization unit and the second crystallization unit is carried out when an enantiomeric excess (ee) in the mother liquors of the first crystallization unit and/or the second crystallization unit is in proximity to an eutectic composition.

10. The method according to claim 1, further comprising an auto-seeding process sub-step, wherein the enantiomer or the racemic compound is selectively dissolved while the temperature in the first crystallization unit and/or the second crystallization unit is increased to a certain temperature T(susp), wherein seeds of the desired enantiomer or of the desired racemic compound will remain not dissolved.

11. The method according to claim 10, further comprising at least one entrainment process sub-step carried out to establish an eutectic composition in the mother liquor of the first crystallization unit and/or the second crystallization unit, wherein no mutual exchange of the mother liquors between the first crystallization unit and the second crystallization unit is carried out.

12. The method according to claim 11, wherein the entrainment process sub-step is carried out after the auto-seeding process sub-step.

13. The method according to claim 1, further comprising at least one entrainment process sub-step carried out to enrich the mother liquors with the enantiomer or the racemic compound and to increase the amount of crystallized enantiomer or of the racemic compound, wherein no mutual exchange of the mother liquors between the first crystallization unit and the second crystallization unit is carried out.

14. The method according to claim 13, wherein the entrainment process sub-step is carried out after the process sub-step of the mutual exchange of the mother liquor between the first crystallization unit and the second crystallization unit.

15. The method according to claim 13, further comprising at least one feeding process sub-step, wherein eutectic feeding material is introduced in the first crystallization unit and/or the second crystallization unit.

16. The method according to claim 15, wherein the feeding process sub-step is carried out after the entrainment process sub-step.

17. The method according to claim 6, wherein the mutual exchange of the mother liquors between the first crystallization unit and the second crystallization unit is carried out by a varying exchange flow rate.

18. The method according to claim 17, wherein the exchange flow rate is controlled by a process parameter, measured in at least one of the mother liquors.

19. The method according to claim 1, wherein the process sub-step of the mutual exchange of the mother liquors between the first crystallization unit and the second crystallization unit is carried out when an enantiomeric excess (ee) in the mother liquor of the first crystallization unit and/or the second crystallization unit is within a range of +/−10 mass-% to the eutectic composition.

20. The method according to claim 1, wherein the process sub-step of the mutual exchange of the mother liquors between the first crystallization unit and the second crystallization unit is carried out when an enantiomeric excess (ee) in the mother liquor of the first crystallization unit and/or the second crystallization unit is within a range of +/−5 mass-% to the eutectic composition.

21. The method according to claim 1, wherein the process sub-step of the mutual exchange of the mother liquors between the first crystallization unit and the second crystallization unit is carried out when an enantiomeric excess (ee) in the mother liquor of the first crystallization unit and/or the second crystallization unit is within a range of +/−2 mass-% to the eutectic composition.

* * * * *